United States Patent [19]
Boesten

[11] 3,971,700
[45] July 27, 1976

[54] PROCESS FOR THE ENZYMATIC RESOLUTION OF DL-PHENYL GLYCINE AMIDE INTO ITS OPTICALLY ACTIVE ANTIPODES

[75] Inventor: Wilhelmus H. J. Boesten, Sittard, Netherlands

[73] Assignee: Stamicarbon B.V., Geleen, Netherlands

[22] Filed: June 5, 1975

[21] Appl. No.: 584,197

[30] Foreign Application Priority Data
June 14, 1974 Netherlands........................ 7407941

[52] U.S. Cl. ..................................... 195/2; 195/29
[51] Int. Cl.² ......................................... C12D 13/06
[58] Field of Search............................. 195/2, 29, 30

[56] References Cited
OTHER PUBLICATIONS

Colwick and Kaplan; *Methods In Enzymology;* vol. II, pp. 91 and 92; 1955.
Greenstein and Winitz, *Chemistry of the Amino Acids;* vol. 3; pp. 1778–1779.

*Primary Examiner*—A. Louis Monacell
*Assistant Examiner*—Robert J. Warden
*Attorney, Agent, or Firm*—Cushman, Darby & Cushman

[57] ABSTRACT

Process for the resolution of DL-phenyl glycine amide through selective enzymatic hydrolysis with amino peptidase especially leucine amino peptidase.

7 Claims, No Drawings

PROCESS FOR THE ENZYMATIC RESOLUTION OF DL-PHENYL GLYCINE AMIDE INTO ITS OPTICALLY ACTIVE ANTIPODES

The invention relates to a process for the resolution of DL-phenylglycine amide.

Racemic phenylglycine may be resolved in its optically active antipodes by conventional processes, involving salt-formation of the phenylglycine or a derivative or precursor thereof with an acid and selective crystallisation or other separating technique.

The object of the invention is a process for the resolution of racemic phenylglycine amide, preferably through selective enzymatic hydrolysis.

It is known that amino acid amides may be hydrolysed selectively by means of an enzyme. Aromatic amino acid amides, such as phenylalanine amide, may in general be hydrolysed under the influence of enzymes, such as papain, bromelain or fycin. Applicant however found that these enzymes do not hydrolyse phenylglycine amide.

It has now been found that D-phenylglycine amide and L-phenylglycine may be prepared starting from racemic phenylglycine amide, the invention being characterised in that DL-phenylglycine amide is hydrolysed by means of a suitable aminopeptidase and that D-phenylglycine amide and/or L-phenylglycine is/are isolated. Said isolation may be carried out by any conventional technique.

Whether or not a given aminopeptidase is suitable may easily be ascertained by a technique as described in the examples.

The preferred enzyme is leucine-aminopeptidase (Enzyme Commission Number 3.4.1.1), which effects highly stereospecific hydrolysis of the racemic amide in a short time.

The reaction may be carried out under conventional conditions, such as described i.a. in Dixon & Webb 'Enzymes' p. 247 (1965) for the hydrolysis of other racemic amino acid amides by means of aminopeptidase enzymes.

Preferably the temperature is maintained at 20°–40 °C and the reaction is effected in a buffered aqueous solution at a pH of between about 7 and 9,5. Activating compounds such as for example manganese salts and magnesium salts may be added.

The processing method for the isolation of the reaction products D-phenylglycine amide and L-phenyl glycine is independent of whether or not use is made of free aminopeptidase or water-insoluble aminopeptidase. Since L-phenyl glycine is poorly soluble in water, the process will have to be effected in dilute solutions when insoluble enzyme is used, in order to prevent crystallization of L-phenyl glycine on the insoluble enzyme. In both variants of the process the L-phenyl glycine can be separated from the D-phenyl glycine amide by extraction, crystallization, or by means of one or more ion exchange resins.

The L-phenyl glycine may be removed as such or after racemization. DL-phenyl glycine may be converted by means of an acid and an alcohol, into the salt of phenyl glycine alkyl ester, which can be treated with ammonia to obtain DL-phenyl glycine amide, which may be returned to the process.

The starting product of the process according to the invention can be prepared from the amino nitrile of phenyl glycine in a known way by acid hydrolysis to form DL-phenyl glycine amide salt, from which the DL-phenyl glycine amide can be obtained by treating it with an equivalent amount of base.

The D-phenyl glycine amide obtained from the processing method can be hydrolysed to D-phenyl glycine salt without racemization, by heating the amide with an aqueous solution of a strong acid such as sulfuric acid, hydrochloric acid, benzensulfonic acid or toluenesulfonic acid.

This salt can be treated with ammonia, whereupon D-phenyl glycine crystallizes in the free form. Thus, the invention also comprises a method for the preparation of D-phenyl glycine, in which DL-phenyl glycine amide is selectively hydrolysed by means of a suitable aminopeptidase, followed by isolation of D-phenyl glycine amide and conversion of this amide to D-phenyl glycine or an acid addition salt thereof.

D-phenyl glycine is used, i.a., as a starting material for the preparation of $\alpha$-amino benzyl penicillin. L-phenyl glycine is used, e.g., as a starting material for L-asparagine-L-phenyl glycine methyl ester (a sweetening agent).

The aminopeptidase may be used in the free or in the insoluble state, e.g. covalently bonded to an insoluble carrier.

The invention will be elucidated with reference to the following examples, but will not be restricted by them.

EXAMPLE 1

3.0 mg moles (560 mg) of DL-phenyl glycine amide.HCl are dissolved at room temperature in 52.0 ml of a buffer solution (boric acidpotassium chloride-sodium hydroxide) with a pH of 9.0 in a reaction vessel provided with a stirrer. After addition of 2.2 ml or 0.125-M $MgCl_2$ and 0.1 ml of 0.025-M $MnCl_2$, the pH is adjusted to a value of 8.5 by means of 2,0 ml of approximately 1-N sodium hydroxide. Next, 0.4 mg of leucine aminopeptidase (80 mg of Merck 25010 enzyme suspension; from pig's kidneys) is added to this solution and stirred at room temperature and a pH of 8.5 for 1.5 hours.

A thin-layer chromatographic analysis shows that the L-phenyl glycine amide has been fully hydrolysed to L-phenyl glycine. After a reaction time of 20 more hours the reaction mixture contains according to an aminoacid analysis: 0.40 % by weight of L-phenyl glycine (efficiency = 100 %) and 0.39 % by weight of D-phenyl glycine amide (yield = 99.5 ).

EXAMPLE 2

A solution of 32.3 mg moles (6.0 grams) of DL-phenyl glycine amide.HCl, 300 mg of $MgCl_2$, and 1 mg of $MnCl_2$ in 80 ml of water is adjusted to an pH of 8.1 by means of 25 ml of approximately 1-N sodium hydroxide in a reaction vessel provided with a stirrer. After addition of 1.5 mg of leucine aminopeptidase (300 mg of Merck 25010 enzyme suspension) to this clear solution, the solution is stirred at room temperature for 4 hours. During the reaction, the pH of the reaction mixture is controlled at a value between 8.1 and 9.1 by means of approximately 1-N hydrochloric acid and an auto-titrator. After this period the pH is adjusted to 6.5 by means of hydrochloric acid and then the reaction mixture is concentrated to a volume of 50 ml by evaporation (30 °C; 12 mm Hg). The crystallized L-phenyl glycine is isolated by filtration. The yield of L-phenyl glycine is 2.0 grams (efficiency = 83.3 %).

Specific rotation of this L-phenyl glycine: $[\alpha]_D^{25} = +156°$ (2.6 % by weight of HCl; C = 1.6).

Reference: Beilstein 14 III p. 1188 $[\alpha]_D^{25} = +157.5°$ (2.6 % by weight of HCl; C = 1.6). Selectivity: % L-phenyl glycine = 99.5.

50 ml of concentrated hydrochloric acid are added to the filtrate and the D-phenyl glycine amide.HCl which then crystallizes is also isolated by filtration.

The yield of D-phenyl glycine amide.HCl is 2.5 grams efficiency 83.6 %). Molar rotation of D-phenyl glycine amide.HCl: $[M]_D^{20} = -186.5°$ (water; C = 0.8).

Reference: Beilstein 14 III p. 1189 $[M]_D^{20} = -188°$ (water; C = 0.8). Selectivity: % D-phenyl glycine amide.HCl = 99.5.

A solution of the resulting D-phenyl glycine amide.HCl in 20 ml of 6-N hydrochloric acid is boiled for 1½ hours. After evaporation to dryness of the reaction mixture, the evaporation residue is absorbed in 20 ml of water. A thin-layer chromatographic analysis of this solution shows that the D-phenyl glycine amide has fully converted to D-phenyl glycine. The pH of the solution is adjusted to a value of 6.5 by means of concentrated ammonia and the crystallized D-phenyl glycine is filtered through a glass filter and washed on the filter with 5 ml of water.

The yield of D-phenyl glycine is 0.35 gram(efficiency = 81 %). Specific rotation of this D-phenyl glycine: $[\alpha]_D^{20} = -147°$ (C = 0.6; 2-N HCl); reference: Beilstein 14 III p. 1187 $[\alpha]_D^{20} = -153°$ (C = 0.6; 2-N HCl). Selectivity: % D-phenyl glycine = 98.

EXAMPLE 3

A solution of 5.0 mg moles (930 mg) of DL-phenyl glycine amide. HCl, 50 mg of $MgCl_2$ and about 0.2 mg $MnCl_2$ in 100 ml of water is adjusted to a pH of 8.0 by means of 1-N sodium hydroxide. After addition to this solution of 250 mg of leucine aminopeptidase (Merck 25010) covalently bonded to 3-amino-propyl-triethoxysilyl Bio-Glass with a load of 0.3 % by weight, obtained as described in Biotechnology and Bioengineering Vol. XVI, pp. 275–77, 1974, the solution was stirred at room temperature for 18 hours.

After filtration of the leucine aminopeptidase bonded to glass powder, the filtrate is subjected to a thin-layer chromatographic examination. This showed that the DL-phenyl glycine amide was converted into equimolar amounts of L-phenyl glycine and D-phenyl glycine amide by leucine aminopeptidase convalently bonded to glass.

The filtrate is adjusted to a pH of 10.0 with 1-N NaOH and then passed over 100 grams of Amberite I.R.C.–50 ion exchanger in the $H^+$ form. Next 100 ml of water is passed over, the ion exchanger, the eluate is evaporated to a volume of 15 ml in vacuo, and the L-phenyl glycine is isolated by filtration. The yield of L-phenyl glycine which is pure according to thin-layer chromatography is 0.34 gram(efficiency 90 %).

Specific rotation of this L-phenyl glycine: $[\alpha]_D^{25} = +157°$ (2.6 % by weight of HCl; C = 1.6). Reference: Beilstein 14 III, p. 1188: $[\alpha]_D^{25} = +157.5$ (2.6 % by weight of HCl; C = 1.6). Selectivity: % of L-phenyl glycine= 99.8 %.

The D-phenyl glycine amide bonded to the Amberlite I.R.C.–50 is extracted with 150 ml of 0.5-N sulfuric acid. The eluate is concentrated to 10 ml by evaporation in vacuo and then boiled for 1 hour. After cooling and neutralization with concentrated aqueous ammonia, the crystallized D-phenyl glycine is filtered over a glass filter and washed on the filter with 5 ml of water. The yield of D-phenyl glycine is 0.33 gram (efficiency 90 %). Specific rotation found:

$[\alpha]_D^{25} = -152°$(C = 0.6; 2-N HCl) Reference: Beilstein 14 III, p. 1187: $[\alpha]_D^{25} = -153°$ (C = 0.6; 2-N HCl). Selectivity: % of D-phenyl glycine = 99.2 %.

EXAMPLE 4

0.5 mg of leucine aminopeptidase (Serva 27717; from ox eyes) is added to a solution of 1.62 mgmoles (0.3 gram) of DL-phenyl glycine amide. HCl, 12 mg of $MgCl_2$ and 0.3 mg of $MnCl_2$ in 35.0 ml of buffer solution (boric acid-potassium chloride-sodium hydroxide) at room temperature and a pH of 8.1 with stirring in a reaction vessel provided with a stirrer. The pH of the reaction mixture rises to 8.6 in a period of 15 minutes and then remains constant. A thin-layer chromatographic analysis shows that the reaction mixture consists of equimolar amounts of L-phenyl glycine and D-phenyl glycine amide after 45 minutes and after 4 hours. An amino-acid analysis carried out after a reaction time of 6 hours gives the same result, viz.:

0.35 % by weight of L-phenyl glycine (yield = 100 %)
0.34 % by weight of D-phenyl glycine amide (yield = 99 %).

EXAMPLE V 1.6 mgmoles (0.3 g) of DL-H-phenyl glycine amide.HCl are dissolved in 30 ml of a buffer solution (boric acid-potassium chloride-sodium hydroxide) at a pH of 7.0. After addition of 1.0 ml of a 0.125 Molar $MgCl_2$ solution and 0.1 ml of a 0.025 molar $MnCl_2$ solution 0.8 mg aminopeptidase M (Enzyme Commission number 3.4.11.2 'particle-bound aminopeptidase' from hog kidney, obtained from Sigma, nr. A-7761) are added. The pH was adjusted to 7.1 and the mixture is stirred during 21 hours. During this period the pH increased gradually to a pH of 7.45.

Samples of the reaction mixture are analysed by thin-layer chromatography. After 2 hours the mixture of amino-acids consists of 3 mole % of phenyl glycine and after 20 hours 50 mole % of phenyl glycine. Stirring is continued. Amino-acid analysis shows 0.34 wt % of phenyl glycine and 0.40 wt % of phenyl glycine amide. After 24 hours and 0.45 wt % of phenyl glycine and 0.35 wt % of phenyl glycine amide after 100 hours. Thus, this enzyme, although not unsuitable, is inferior to the leucine aminopeptidase used in the previous examples.

What is claimed is:

1. A process for preparing D-phenyl glycine amide and L-phenyl glycine, comprising hydrolyzing DL-phenyl glycine amide with an aminopeptidase and isolating D-phenyl glycine amide, L-phenyl glycine, or both by conventional techniques.

2. The process according to claim 1, wherein said aminopeptidase is leucine aminopeptidase.

3. The process according to claim 1, wherein said step of hydrolyzing is effected at a pH of 7–9.5 and a temperature of 20° to 40°C.

4. The process according to claim 1, wherein said aminopeptidase is used in an insoluble form.

5. The process according to claim 1, wherein D-phenyl glycine amide is separated and said amide is converted into D-phenyl glycine.

6. The process according to claim 5, wherein the amide is converted into D-phenyl glycine by treating the amide with an aqueous solution of a strong acid.

7. The process according to claim 6, wherein said acid is sulfuric acid, hydrochloric acid, benzene sulfonic acid or toluene sulfonic acid.

* * * * *